United States Patent
Eftekhari

(10) Patent No.: US 9,709,486 B2
(45) Date of Patent: Jul. 18, 2017

(54) METHOD OF DYNAMIC SPECTROSCOPY UNDER PHYSIOLOGICAL CONDITIONS

(71) Applicant: INOVIEM SCIENTIFIC, Illkirch Graffenstaden (FR)

(72) Inventor: Pierre Eftekhari, Strasbourg (FR)

(73) Assignee: INOVIEM SCIENTIFIC, Illkirch Graffenstaden (FR)

( * ) Notice: Subject to any disclaimer, the term of this patent is extended or adjusted under 35 U.S.C. 154(b) by 24 days.

(21) Appl. No.: 14/386,968

(22) PCT Filed: Mar. 22, 2013

(86) PCT No.: PCT/EP2013/056171
§ 371 (c)(1),
(2) Date: Sep. 22, 2014

(87) PCT Pub. No.: WO2013/139988
PCT Pub. Date: Sep. 26, 2013

(65) Prior Publication Data
US 2015/0050272 A1    Feb. 19, 2015

(30) Foreign Application Priority Data

Mar. 22, 2012    (EP) .................................... 12360022

(51) Int. Cl.
*G01N 21/62*    (2006.01)
*G01N 21/359*    (2014.01)
(Continued)

(52) U.S. Cl.
CPC ....... *G01N 21/359* (2013.01); *A61K 39/3955* (2013.01); *G01N 33/6845* (2013.01);
(Continued)

(58) Field of Classification Search
None
See application file for complete search history.

(56) References Cited

U.S. PATENT DOCUMENTS 5,729,333 A * 3/1998 Osten ................. A61B 5/14535
356/39
2007/0211247 A1   9/2007 Tsenkova

FOREIGN PATENT DOCUMENTS

CN         1401988 A     3/2003
CN      101238224 A     8/2008
(Continued)

OTHER PUBLICATIONS

Segtnan, V.H. et al. Temperature, sample and time dependent structural characteristics of gelatine gels studied by near infrared spectroscopy, 2004, Food Hydrocolloids, vol. 18, pp. 1-11.*

(Continued)

*Primary Examiner* — Robert Xu
(74) *Attorney, Agent, or Firm* — Buchanan Ingersoll & Rooney PC

(57) ABSTRACT

The present invention relates to the field of dynamic spectroscopy and more precisely to a method involving dynamic molecules spectroscopy technology designed to determine transitional changes in molecules conformation and assemblies both in physiologic and pathologic conditions. The method comprises in vitro fingerprints of a sample taken under highly controlled temperature in order to obtain precise images of either one or an ensemble of molecular dynamics. Due to its precise information, the method according to the invention allows shortening of the drug discovery stage.

17 Claims, 10 Drawing Sheets

(51) Int. Cl.
  *A61K 39/395*   (2006.01)
  *G01N 33/68*    (2006.01)
  *G01N 33/94*    (2006.01)

(52) U.S. Cl.
  CPC ......... *G01N 33/94* (2013.01); *G01N 2500/04* (2013.01); *G01N 2800/52* (2013.01)

(56) References Cited

FOREIGN PATENT DOCUMENTS

JP        2008545437 A    12/2008
SE    WO 2008/115120    *   9/2008   ......... G01N 33/483
WO      2005050176 A1    6/2005

OTHER PUBLICATIONS

Murkin, J.M. et al. Near-infrared spectroscopy as an index of brain and tissue oxygenation, 2009, Brithish Journal of Anaesthesia, vol. 103, pp. i3-i13.*

Vanderkooi, Jane M., Jennifer L. Dashnau, and Bogumil Zelent. "Temperature excursion infrared (TEIR) spectroscopy used to study hydrogen bonding between water and biomolecules." Biochimica et Biophysica Acta (BBA)-Proteins and Proteomics 1749.2 (2005): 214-233.

Japanese Office Action (Notification of Reasons for Refusal) mailed Mar. 1, 2016 in counterpart Japanese Patent Application No. 2015-500949, with English machine translation (7 pages).

Chinese Office Action ("Notification of First Office Action") mailed May 5, 2016 in counterpart Chinese Patent Application No. 201380026932.7, with English translation (14 pages).

* cited by examiner

METHOD OF DYNAMIC SPECTROSCOPY UNDER PHYSIOLOGICAL CONDITIONS

The present invention relates to the field of dynamic spectroscopy and more precisely to a method involving dynamic molecules spectroscopy technology designed to determine transitional changes in molecules conformation and assemblies both in physiologic and pathologic conditions. The method comprises in vitro fingerprints of a sample taken under highly controlled temperature in order to obtain precise images of either one or an ensemble of molecular dynamics. Due to its precise information, the method according to the invention allows shortening of the drug discovery stage.

Determination of molecular interactions and especially protein-protein interactions has been one of the major challenges for pharmaceutical companies during the past two decades. In fact, drug development is facing its less innovative and therefore less productive period. The success of a drug discovery program relies on the wealth and accuracy of knowledge obtained from basic research, target validation, etc. The basic research is dependent on pertinence as well as limits of the method, tools and technologies used to solve biological problems. The fact that the drug discovery and development is stagnant shows the failure of available methods and technologies to meet the therapeutic needs. Furthermore, current drug development schemes are too long and costly.

There are several reasons explaining the interest of the pharmaceutical companies for the protein-protein interaction study and the main ones are allowing the identification of proteins involved in particular activity of function of a living organism and, determining the corresponding target and therefore the corresponding receptor, then identifying and validating said therapeutic target, the pharmacophores and finally designing and developing molecules able to bind the identified receptor, optimization of the lead compound and finally development of drug candidates. This is a classical drug discovery and development scheme. In fact all information needed to build up a drug development strategy comes from indirect exploration methods where the native targets are replaced by copies or partially identical structures. All of them are based on modified targets that are modified either genetically or chemically, i.e. purified protein, protein chimera, mutated protein, conjugates, knock out, etc. None of these methods and highly sophisticated technologies considers the living organism in a holistic way. Instead they are all focused on a particular target in a very specific signaling cascade and this is valid for both in vitro and in vivo studies.

Unfortunately, outcomes of such a huge research and development effort remain very small and in some cases it fails due to several problems such as target validation, lead optimization, etc. Many fails are due to the use of techniques that are not adapted to the case or the use of too simple physiological but validated study models. Moreover many steps, well adapted or not, aligned in cascade, are based only on the efficiency of the previous step. Consequently the uncertainties or approximations lead to fails.

In addition, the pharmaceutical industry is facing new demands for which the classical drug development remains inefficient and somehow a drawback for development of new treatments. The physicians seem more focused on preventive and therapeutic medicine than on symptomatic treatment. It is a need for new methods and technologies to study and understand the pathophysiology of a given disease. It is also a need for methods which outcome give accurate information on nature of molecular interactions, allow identification of different molecular actors, allow identification of target receptor(s), and allow selection of specific ligands with beneficial therapeutic effect. Ideally said methods are complementary and not dependent from each other to overcome the drawbacks of prior art.

As an example of prior art we can mention the methods of spectroscopy using near infrared emitting labels such as fluorophores as the one described in Wubiao D. et al (Organic & Biomolecular Chemistry, 2005, vol. 3, n° 13) or Tung C H. et al (Chembiochem, 2003, 4(9):897-9). Such techniques involve at least a step of labeling of the molecule of interest and it results in the abolition of physiological conditions for the sample containing the molecule of interest. As another example of prior art we can mention the patent application published as EP23566467 that describes a method of detection of physiologically acceptable polymer molecules using near infrared spectroscopy. Said method is based on the detection of the amount of a polymer bound on a protein of interest using near infrared spectroscopy and the measurement of the number of polymer moieties per protein molecule allows for production of molecules having a uniform number of polymer moieties, which is useful in the production of pharmaceutical compositions. The results are obtained when compared to a previously calculated standard having a known amount of polymer molecules conjugated to a protein of interest. Said method involves purification and concentration of the protein of interest so the physiological conditions are abolished and another drawback is that a reference or standard is needed to proceed with a conclusion to the study. Besides this method is based on NIR spectra of fluorophores and not on the surrounding environment of the protein of interest.

The patent application WO2008/115120 describes a method to detect binding and reactions of substances in an aqueous sample, wherein the binding or reaction changes the spectroscopic properties of water, and the binding or reaction is detected by observing or measuring any change in the spectroscopic properties of water. This document relates only to a concept since no method is fully described nor illustrated by data. Moreover, the method of WO2008/115120 is not dependent on any particular detection means for measuring the change in spectroscopic properties and uses equally infrared, Raman, terahertz, sum frequency generation, or photoacoustic spectroscopy, or vibrational circular dichroism.

There is urgent need for a more efficient basic and translational development strategy to overcome the aforementioned drawbacks. Ideally the new method should be based on one step exploration technology where its outcome reflects the living behaviour of a molecule or an ensemble of molecules against a particular stimulus or several stimuli. It should also be an in vitro signature as precise as the one obtained in human both in normal and pathologic conditions. Finally said method should consider all the changes induced in a living organism after a given stimulus and not just a selected reaction, such as an isolated signal, within a whole signaling cascade.

The present invention relates to a method of conformational analysis of a sample containing a biological molecule of interest wherein said analysis is made by spectroscopic analysis near infrared wavelength of water molecules surrounding the molecule of interest. The spectroscopy analysis results in a fingerprint or spatial print of the molecule of interest materialized by graphics or three-dimensional images further to data sampling and processing. The present invention relates also to a method for providing in vitro fingerprints of molecules, said fingerprints representing in vivo molecular interactions in physiologic and pathologic conditions. The method of the invention can be applied to molecules, macromolecules, proteins, protein complexes, glycoproteins, lipoproteins, one or multiple assemblies of at least one or more and either two or more nucleic acid, DNA, all known forms of RNA, protein glycoprotein lipoprotein in presence or absence of vitamins, trace elements, cAMP, ADP, ATP, cGMP, GDP, GTP, NADH, NADPH, FAD, FADH2 or any other molecule involved in native molecular interaction in a given cell, a tissue, an organ or an organism to meet physiological need or participate in pathophysiology of a disease.

In fact, molecular interactions follow the thermodynamic law. This means that all interactions either within a molecule or in relation to its environment or another molecule within the same environment strive to reach the lowest energy state. That is to say going from highest metastable energy state to lowest metastable energy and finally reaches the stable state. The latter is known as molecular auto-assembly theory. Molecular interactions within a living cell, although bound to the very same thermodynamic law, do not follow the auto-assembly theory. All thanks to ATP. Thermodynamic molecular interactions together with ATP are the main actors to insure the cellular activity and therefore the maintenance of its physiology. The cascades of molecular interactions are multiple and transitory. All the actors within a signaling cascade change their conformation constantly both intrinsically and in relation with surrounding molecules. This explains the transition of their role as a signaling cascade evolves. In a fraction of time, a given protein plays the role of receptor and in another fraction it becomes a structural partner or stands for the role of effector. These rapid transitions must be taken into account when designing new study methods and developing adapted technologies.

In the prior art, three-dimensional molecules analyses are made by spectrometry in a wavelength range between 260 nm and 280 nm. The resulting image depends on the light absorption on the aromatic aminoacids. When the wavelength is higher there is no more absorption, so no more information. In the infrared range, the resulting image depends on the carbon atoms absorption. All known methods, such as crystallography and magnetic nuclear resonance, need purified samples or special conditions such as the dilution in organic solvents. They all result in three-dimensional images and consequent analyses, but none of them can be made in physiological conditions.

As detailed above, following the biological molecules conformations in physiological conditions using spectrometry techniques in the near infrared range is not known in the prior art. The advantage of working within the near infrared range is that it allows the measurement of the water molecules light intensity transmission. And thanks to analysis of such data, and after data processing, obtaining graphics and three-dimensional images showing the spatial fingerprint of the molecule(s) that is(are) surrounded by said water molecules. The present invention is based on the observation of the conformational equilibrium situations between the water molecules and its various partners in different situations. The present invention gives dynamic fingerprints, or spatial prints of water molecules, and consequently allows the interpretation of the interactions between the molecules surrounded by the observed water molecules.

The most important molecule necessary for all molecular interactions in physiological conditions is water. Its presence around the macromolecules as medium and within the proteins as partner makes the molecular interaction not only possible but also dynamic. This means that in its absence all interaction would stop. This would also happen if water molecules lose their resonance and intrinsic action. This can happen when the water is frozen. In this case water crystals make the perfect medium for taking macromolecular fingerprints. These could be taken at constant temperature thus having a stable fingerprint or at different temperatures thus obtaining a dynamic fingerprint.

The in vitro fingerprints according to the invention are taken based on dynamic conformations of water molecules going from metastable to stable and again metastable conformations, under highly controlled temperature, going step wise from −37° C. to 37° C. and return, in constant resonance. The fingerprints are taken in their physiological conformations in presence of physiological medium, i.e. identical as the one within a living cell with comparable anions, cations, trace elements, vitamins, proteins, glycoproteins, lipoproteins, lipids, sugar, nucleic acids, in short the entire cytoplasm.

The present invention provides a method for obtaining the fingerprint of at least one biological molecule of interest in a sample using spectroscopy under physiological conditions, comprising:
  a) exposing the sample to a light source in the near infrared spectrum,
  b) measuring the light intensity transmission of water molecules surrounding the biological molecule of interest,
  c) determining the fingerprint of said biological molecule of interest.

In a first embodiment the method of the invention is used with increasing wavelengths in a range of near infrared wavelengths. In a second embodiment the method of the invention is made at a given wavelength selected in the near infrared range of wavelengths.

The present invention is based on the aforementioned principle and relates to a method for providing in vitro dynamic molecular fingerprints wherein said method comprises the steps of:
  preparing a sample with a molecule of interest;
  using classic spectroscopy techniques at near infrared wavelength to study the dynamic changes of the molecule of interest;
  exposing said sample under light scattering and under highly controlled temperature, from a physiological temperature of 37° C. to a negative temperature and back to the initial temperature, based on the constant resonance of the light source and the detector;
  building up a three-dimensional image after data sampling and processing and also graphic analysis;
wherein the light source, the thermo-regulator, the sample support, the optical system and the detector are all placed in relative vacuum in a vacuum chamber.

The light intensity transmission by the water molecules surrounding the molecule of interest can be influenced by absorption of light or by diffraction of light by the water molecules and their organisation. When experimental parameters are changing, such as temperature, the network of water molecules will also change and the bounds between water molecules and the molecule of interest also.

The terms defined below can be singular or plural and when used herein have the same sense as the one detailed below.

The term "sample" as used herein refers to any sample containing at least one molecule of interest. The sample can be in solution or not. Without any limitation, such a sample can be a vegetal tissue, an animal tissue, or human tissue, a vegetal organ, an animal organ, a human organ, a microorganism, a cell culture, a cell colony, a cell suspension, a cell extract, a cancerous cell, a nucleic acid or nucleic acids, or any part or extract thereof, or any preparation thereof.

The term "molecule of interest" as used herein refers to a molecule, a macromolecule, a protein, a protein complex, a glycoprotein, a lipoprotein, one or more multiple assemblies of at least one nucleic acid, DNA, all known forms of RNA, in presence or not of vitamin, trace elements, cAMP, ADP, ATP, cGMP, GDP, GTP, NADH, NADPH, FAD, FADH2 or any other molecule involved in native molecular interaction in given cell, tissue, organ or organism to meet physiological need or participate, one way or another in pathophysiology of a disease.

The terms "fingerprint" or "spatial print" or "print" as used herein refers to the visual representation, such as graphics or three-dimensional images, of a spatial print of the molecule of interest. More precisely, by spatial print is meant a set of data and/or measurements of light absorbance at various wavelengths in the near infrared range. Such molecule of interest being bounded or not, assembled or not, interacting or not, with test compounds or test tissues, etc.

The term "surrounding" as used herein refers to the fact of being adjacent to the molecule of interest, in contact or not with said molecule of interest or interacting or not with said molecule of interest, or bounded or not to the molecule of interest. Such molecules in a sample according to the invention are typically water molecules.

The term "spectroscopy" as used herein refers to the measurement of light intensity transmission of molecules of water surrounding the molecule of interest, as a function of wavelength. More specifically, near-infrared (NIR or NIRS) spectroscopy is the measurement of the wavelengthh and intensity of the absorption of near-infrared light by a sample. Near-infrared light spans the range from 800 nm-2.5 µm (12,500-4000 cm-1) and is energetic enough to excite overtones and combinations of molecular vibrations to higher energy levels. The method of the present invention uses the differential absorption and/or diffraction properties of rater molecules surrounding the molecule of interest.

The term "dynamic spectroscopy" or "dynamic fingerprint" as used herein refers to the result of a comparison between spectroscopy outcomes such as fingerprints described above, three-dimensional images or graphics in order to assess the evolution of the conformation of the molecule of interest in different conditions of temperature. According to the present invention, the dynamic spectroscopy allows the study of molecular dynamic, macromolecular dynamics, molecular complex, macromolecular complex, protein conformation, protein-protein interactions, protein complex, homo-dimerisation, hetero-dimerisation, homo-oligomerisation, hetero-oligomerisation, ligand protein interaction, ligand interactome interaction whereas the ligand is a natural ligand, biologic ligand or exenobiotics thereof, whereas the exenobiotic is natural or synthetic, on any extract from living cell, organ, organism whereas the organism is eukaryote, prokaryote or plant.

The term "test molecule" as used herein refers to an isolated molecule. It can be a natural molecule, a synthesized molecule, of any size and nature. Said test molecule can be purified or not.

The term "putting in contact" refers to a spatial contact, with or without interaction, but also to a mixture of the concerned components.

In a preferred embodiment, the method according to the invention provides dynamic molecular fingerprints taken from a physiological temperature near 37° C. to a very low temperature such as −37° C. and back to the physiological temperature of 37° C. This means that the entire macromolecular interactions isolated as such from a given living cell or organ are snap frozen to −37° C. and thawed step wise one degree at the time to 37° C.

The present invention describes a method for providing in vitro dynamic molecular fingerprints wherein said method comprises the steps of:
  preparing a sample with a molecule of interest;
  using classic spectroscopy techniques at near infra red wavelength to study the dynamic changes of the molecule of interest;
  exposing said sample under light scattering and under highly controlled temperature from 37° C. to −37° C. and back to 37° C. based on the constant resonance of the light source and the detector;
  building up a three-dimensional image after data sampling and processing and also graphic analysis;
  wherein the light source, the thermo-regulator, the sample support, the optical system and the detector are all placed in relative vacuum in a vacuum chamber.

The method of the invention is used in the near infrared spectrum corresponding to the range of wavelengths from 680 nm to 2500 nm, preferentially from 900 nm to 1410 nm.

In a particular embodiment, the method according to the invention provides dynamic molecular fingerprints taken using spectroscopy technique at near infra red wavelength, i.e. from 900 nm to 1410 nm, or at fixed wave length in the same wave length range, with a continuous read out at each degree from 37° C. to −37° C. and return. The present invention relates to a method for obtaining a fingerprint of a biological molecule of interest as detailed above where the wavelength range is between 680 nm and 2500 nm, preferentially from 900 nm and 1410 nm. In another embodiment the method according to the invention is made at a fixed wavelength selected in the near infrared range, this means a wavelength comprised between 680 nm and 2500 nm, more preferentially between 900 nm and 1410 nm.

In another embodiment, the dynamic molecular fingerprint of the invention is taken when the sample is placed between a laser or visible light source and the detector, while they are in constant horizontal resonance with adjustable resonance speed. Consequently, the present invention relates to a method for obtaining a fingerprint as detailed above where the light source is visible light, halogen or laser.

According to the present invention the dynamic molecular fingerprint is taken through light scattering on the sample from 37° C. to −37° C. and back to 37° C., based on the resonance of the light source and the detector, which is processed to build up a three-dimensional image showing the fine conformational evolution of macromolecules imbedded in physiological presence of water molecules. In a first embodiment the invention relates to a method for obtaining fingerprint of a biological molecule of interest, wherein the fingerprint consists of a three-dimensional image. In a second embodiment the invention relates to a method, wherein the fingerprint consists of a graphic representation.

In a particular embodiment, the method according to the invention involves that several fingerprints of a same sample are taken at different temperatures and compiled to deduct a dynamical conformational comportment of the biological molecule of interest. In another particular embodiment said fingerprints of the molecule of interest are taken at various temperatures among which positive and negative temperatures in Celsius degrees. In yet another embodiment the different fingerprints of a same sample are measured within a temperature range between −37° C. and 37° C., preferentially in a temperature range from 37° C. to −37° C. and back to 37° C. In a preferred embodiment, one fingerprint according to the invention is realized for each integer degree of the selected temperature range.

The method of the invention allows the analysis of various molecules of interest among which macromolecule, protein, protein complex, glycoprotein, lipoprotein; one or multiple assemblies of at least one or more, either two or more nucleic acid, DNA, all known forms of RNA, protein, glycoprotein, lipoprotein in presence or absence of vitamins, trace elements, cAMP, ADP, ATP, cGMP, GDP, GTP, NADH, NADPH, FAD, FADH2 or any other molecule involved in native molecular interaction in given cell, tissue, organ organism to meet physiological need or participate, one way or the other in pathophysiology of disease. Consequently, the present invention relates to a method of conformational analysis providing in vitro dynamic molecular fingerprints as detailed above where the molecule of interest is a macromolecule, a protein, a protein complex, a glycoprotein, a lipoprotein, one or more multiple assemblies of at least one nucleic acid, DNA, all known forms of RNA, in presence or not of vitamin, trace elements, cAMP, ADP, ATP, cGMP, GDP, GTP, NADH, NADPH, FAD, FADH2 or any other molecule involved in native molecular interaction in given cell, tissue, organ or organism to meet physiological need or participate, one way or another in pathophysiology of a disease.

The method according to the present invention allows the study of molecular dynamic, macromolecular dynamics, molecular complex, macromolecular complex, protein conformation, protein-protein interactions, protein complex, homo-dimerisation, hetero-dimerisation, homo-oligomerisation, hetero-oligomerisation, ligand protein interaction, ligand interactome interaction whereas the ligand could be a natural ligand, biologic ligand or exenobiotics thereof, whereas the exenobiotic can be natural or synthetic, on any extract from living cell, organ, organism whereas the organism is eukaryote, prokaryote or plant. The present invention relates to the use of the method as described above for the study of molecular dynamic, macromolecular dynamics, molecular complex, macromolecular complex, protein conformation, protein-protein interactions, protein complex, homo-dimerisation, hetero-dimersation, homo-oligomerisation, hetero-oligomerisation, ligand protein interaction, ligand interactome interaction, on any extract from living cell, organ, organism whereas the organism is eukaryote, prokaryote or plant.

The present invention describes an in vitro method for identification of a patient sensitivity to a treatment with a given drug, said method comprising the following steps:
  a) dividing a sample of a patient suspected to suffer or being prone to suffer from a given disease, in two subsamples A and B,
  b) determining the fingerprint of subsample A according to the methods of the invention,
  c) putting in contact subsample B with the given drug,
  d) determining according to the method of the invention the fingerprint of subsample obtain through step c),
  e) determining that the patient is sensitive to the given drug if the fingerprint obtained in d) shows a change of individual macromolecular volume relative to the control level determined in b).

The invention also relates to a method of identifying biomarkers relating to a selected disease and/or disorder. In fact, the pathophysiology of certain diseases and/or disorders varies between patients. When a known drug with proven clinical effect on a disease and/or disorder is used for the treatment and/or prophylaxis of a patient in need thereof, all the patients won't respond to said treatment in the same way, some won't even respond at all. One object of the present invention is to allow the quick identification of the responsive patients and then allow the adjustment of the treatment to each patient according to the progression of the disease and/or disorder by follow-up of one or several biomarkers.

The present invention describes a method for selecting at least a biomarker indicative of a patient sensitivity to a treatment with a given drug, comprising:
  a) determining a group of patients sensitive to the given drug according to the method described above,
  b) determining a group of patients non-sensitive to the given drug according to the same method as in a),
  c) measuring various biomarkers in the patients of group a),
  d) measuring various biomarkers in the patients of group b),
  e) selecting at least a biomarker for which the measure under c) increases or decreases in comparison with the measure under d) as a biomarker indicative of a patient sensitivity to a treatment with said given drug.

In a further embodiment, the invention provides a method for improving treatment effect in a patient suffering from a given disease, said method consisting in:
  (a) determining a patient's sensitivity to a given drug according to any of the methods described above with regards to patient's sensitivity or biomarker identification; and
  (b) administering said given drug to said patient.

The invention is illustrated by the following figures that are not limitative of the scope of the invention.

FIG. 1 is a schematic representation of the instrumental set up for performing dynamic protein spectroscopy in physiological conditions. The light source, the thermoregulator, the optical system and the detector are all placed in relative vacuum in a vacuum chamber. The data sampler and processor is outside said vacuum chamber and the outcome are graphic analysis and three-dimensional images.

FIG. 2 shows dynamic changes of protein conformations in rat hypothalamus extracts with three different dilutions according to various near infrared wavelength (from 1200 to 1450 nm) at 37° C.

FIG. 3 shows dynamic changes of protein conformations in rat hypothalamus extracts with three different dilutions according to various near infrared wavelength (from 1200 to 1450 nm) at −37° C.

FIG. 4 shows protein assemblies in rat hypothalamus extracts with three different dilutions according to various near infrared wavelength (from 1200 to 1450 nm) at −25° C.

FIG. 5 shows protein assemblies in rat hypothalamus extracts with three different dilutions according to various near infrared wavelength (from 1200 to 1450 nm) at −15° C.

FIG. 6 shows protein assemblies in rat hypothalamus extracts with three different dilutions according to various near infrared wavelength (from 1200 to 1450 nm) at −5° C.

FIG. 7 shows protein assemblies in rat hypothalamus extracts with three different dilutions according to various near infrared wavelength (from 1200 to 1450 nm) at 5° C.

FIG. 8 shows protein assemblies in rat hypothalamus extracts with three different dilutions according to various near infrared wavelength (from 1200 to 1450 nm) at −15° C.

FIG. 9 shows protein assemblies in rat hypothalamus extracts with three different dilutions according to various near infrared wavelength (from 1200 to 1450 nm) at 37° C.

FIG. 10 shows the spectral evolution of protein assemblies according to the variation of temperature from 37° C. to −37° C. and back to 37° C.

FIG. 12 shows protein assemblies from different human brain structures in presence of atropine at 37° C.

FIG. 13 shows protein assemblies from different human brain structures in presence of atropine at −37° C.

FIG. 14 shows protein assemblies from different human brain structures in presence of atropine at −7° C.

FIG. 15 shows protein assemblies from different human brain structures in presence of atropine at 7° C.

FIG. 16 shows protein assemblies from different human brain structures in presence of atropine at 37° C.

Figure 1:
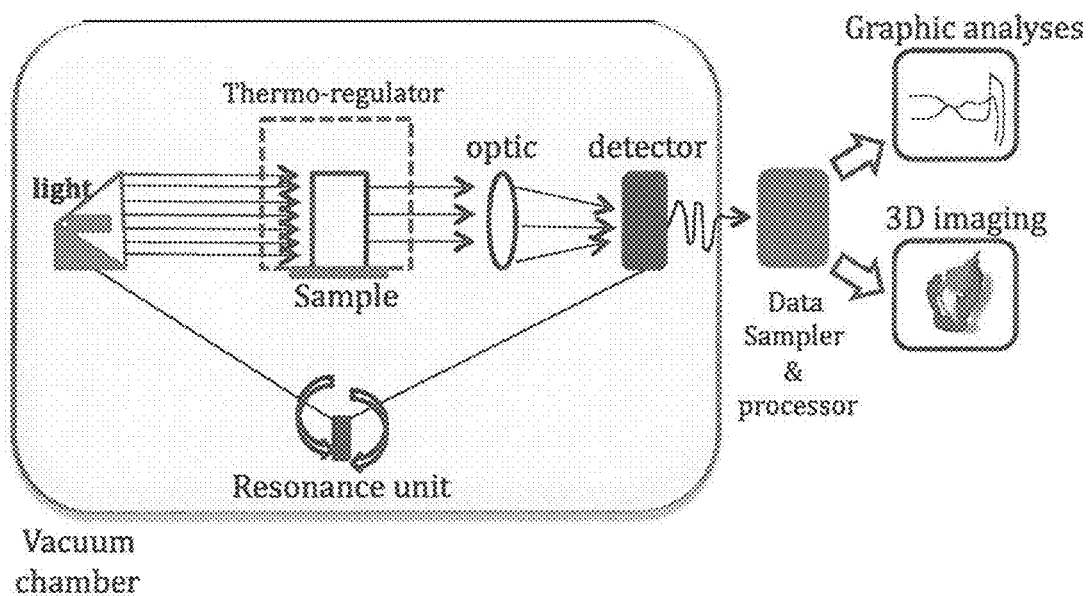

The present invention provides also a method for the determination of the conformation of at least one biological molecule in a sample using spectroscopy under physiological conditions, comprising:
  a) determining the fingerprint of the biological molecule of interest according to the method described above, and
  b) determining from the result of step a) the conformation of said molecule of interest.

In a particular embodiment said method for the determination of the conformation of biological molecules involves that different fingerprints are realized on a same sample at various temperatures, said fingerprints being compiled to deduct a dynamical conformational comportment of the biological molecule of interest.

In yet another embodiment the present invention provides a method for the determination of biological activity of at least one molecule of interest, comprising:
  a) putting in contact the sample with a test molecule,
  b) determining the fingerprint of the sample containing the test molecule as defined in a) according to the method detailed above,
  c) repeating step a) and b) with at least two different samples;
  d) comparing the fingerprints obtained in b) and c), and
  e) deducting the biological activity of the molecule of interest.

In a further embodiment, the method for the determination of biological activity detailed above comprises a further step and consists in:
  a) determining a fingerprint of the test molecule in solution according to the method described above;
  b) putting in contact the sample with a test molecule;
  c) determining the fingerprint of the sample containing the test molecule as defined in a) according to the method described above and used in a);
  d) repeating step b) and c) with at least two different samples;
  e) comparing the fingerprints obtained in a), b) and c); and
  f) deducting the biological activity of the molecule of interest.

In a preferred embodiment, the sample is a tissue or an organ extract. It can be used directly without any step of purification, concentration or labeling.

Such a method allows the observation of the interaction of a test molecule and the tissue and/or organ under physiological conditions. In yet another embodiment such method is applied to various tissue or organ extracts, for example brain extracts such as cerebellum, hippocampus, occipital lobe, parietal cortex, in order to obtain a fingerprint of the test molecule in each brain extract. In a preferred embodiment said fingerprints are taken at various temperatures, preferentially such temperatures are selected among positive and negative temperatures in Celsius degrees. This allows visualizing the assemblies between the test molecule and components of the brain extract or specific brain extracts. It allows also seeing if there are no such assemblies. This gives information about a potential biological effect of the test molecule with respect to each of the tested brain extract.

In a further embodiment the invention provides a method for the determination of the biological activity of at least one molecule of interest according to the embodiments described above, comprising the steps of:
  a) putting in contact the sample with a test molecule,
  b) determining the conformation of the sample containing the test molecule as defined in a) according to the method above,
  c) repeating step a) and b) with at least two different samples;
  d) comparing the conformations obtained in b) and c), and
  e) deducting the biological activity of the molecule of interest.

In yet another embodiment the invention provides a method for the determination of the biological activity of at least one molecule of interest according to the embodiments described above, comprising the steps of:
  a) determining the conformation of the test molecule in solution according to the method described above;
  b) putting in contact the sample with a test molecule;
  c) determining the conformation of the sample containing the test molecule as defined in a) according to the method above,
  d) repeating step b) and c) with at least two different samples;
  e) comparing the conformations obtained in a), c) and d), and
  f) deducting the biological activity of the molecule of interest.

In one embodiment atropine is the test molecule and the test tissue is a brain extract. In a particular embodiment, the method of the invention comprises the following steps:
  a) putting in contact the sample with atropine,
  b) determining the fingerprint of the sample containing atropine as defined in a) according to the method described above,
  c) repeating step a) and b) with at least two different samples;
  d) comparing the fingerprints obtained in b) and c), and
  e) deducting the biological activity of atropine.

Such a method allows the observation of the interaction of atropine and the brain extract under physiological conditions.

In another embodiment such method is applied to various tissue and/or organ extracts, for example brain extracts such as cerebellum, hippocampus, occipital lobe, parietal cortex, in order to obtain a fingerprint of atropine in each brain extract. In a preferred embodiment said fingerprints are taken at various temperatures, preferentially such temperatures are selected among positive and negative temperatures in Celsius degrees.

It allows visualizing the assemblies between atropine and components of the brain extract or specific brain extracts. It allows also seeing if there are no such assemblies. This gives information about a potential biological activity of atropine with respect to each of the tested brain extract.

More details about application of the method of the invention to atropine is given below in the example part.

In a preferred embodiment, the method according to the present invention described above is implemented under highly controlled temperature from 37° C. to −37° C. and back to 37° C. based on the constant resonance of the light source and the detector.

Such a method allows the identification of ligands for receptors of interest and consequently the participation to the drug research and development process.

All the examples and figures are detailed in order to explain the invention and its several steps. They are not limitative of the scope of the present invention.

EXAMPLES

All chemicals used hereafter are commercialized by Sigma Aldrich®. The spectroscopy is performed on a modified version of Cary 5000 doubled sample spectrophotometer with infrared sampling capacity. The material is a monochromator UV-Vis 1200 lines/mm blazed at 250 nm and for NIR (for near infrared) 800 lines/mm blazed at 800 nm, and a detector NIR Cooled InGaAS (for indium gallium arsenide).

1) MEMBRANE PREPARATION

Post-mortem human brain or rat whole brain is/are isolated from male Wistar rats and transferred immediately into an ice cold TRIS, EDTA buffer solution. Either whole brain or cerebellum, hippocampus, hypothalamus/thalamus, neocortex, prefrontal cortex and striatum separately were homogenate in the same before subjecting to 3 successive snap freeze and thawing cycles in liquid nitrogen and 4° C. respectively. There were thereafter centrifuged at 6500 xg for 20 minutes at 4° C. Total protein concentration was determined using BCA protein assay methods, and stored at −20° C. until use. Each fraction was thawed only once for each experiment series.

2) DYNAMIC SPECTROSCOPY

All experiment is performed in comparison with the solvent (S) or the reference molecule, in all different conditions. The presented charts are subtracted from the blank (solvent) and reference molecule.

For dilution experiments total isolate protein is used at concentrations of $10^{-3}$, $10^{-6}$ and $10^{-9}$ mg/ml. For experiments on different brain structures samples are diluted at $10^{-6}$ mg/ml. For experiments with test molecules samples are used at concentration $10^{-6}$ mg/ml. All experiments are performed at the volume of 110 µl. Sample buffer constituted the blank. For the experiment with test molecules atropine and biothinol, 10 µl at final concentration of 1 µM was added to the test sample. The bland was constituted of 1 µM of test molecule in sample buffer. Briefly total protein at above mentioned concentrations and volume as well as blank was snap frozen at −37° C. The dynamic spectral samples were taken between 900-1410 nm for 35 second each, from −37° C. gradually to 37° C., with either 7 or 10 degrees increasing temperature intervals, depending on the experiment set up.

3) RESULTS

Dynamic change in rat hypothalamus extracts protein conformations with 3 different dilutions are shown in FIGS. 2 to 10.

Figure 2:
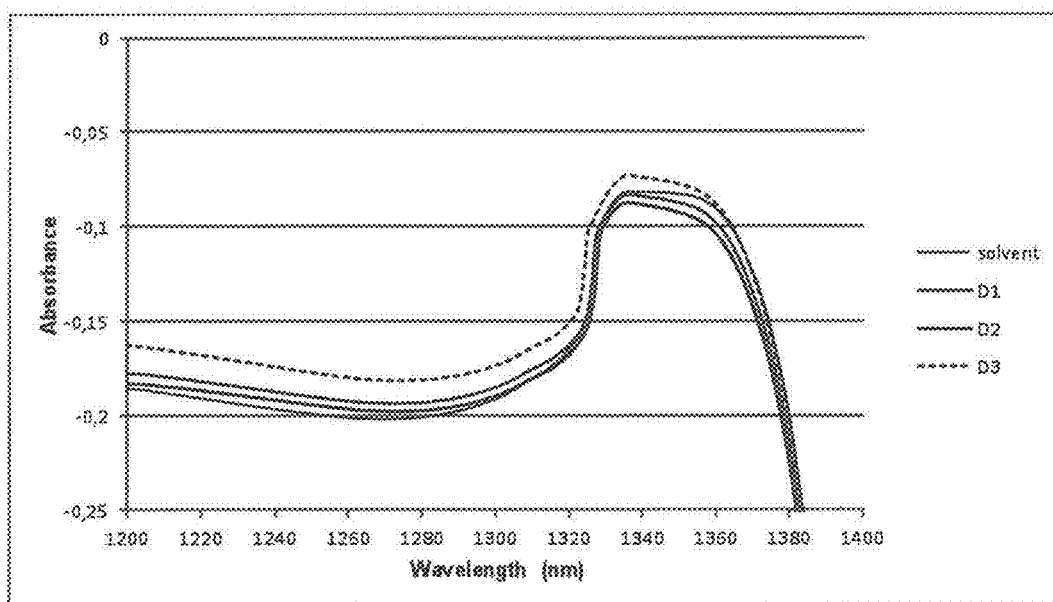
FIGS. 2 to 10 show results on rat hypothalamus extract in physiological conditions.

In FIG. 2 The absorbance peak at 1340 nm shows no difference between different protein concentrations. The overall absorbance spectra are identical, indicating that at normal physiological temperature the differences in molecular fingerprints between the various conditions are not noticeable.

Figure 3:
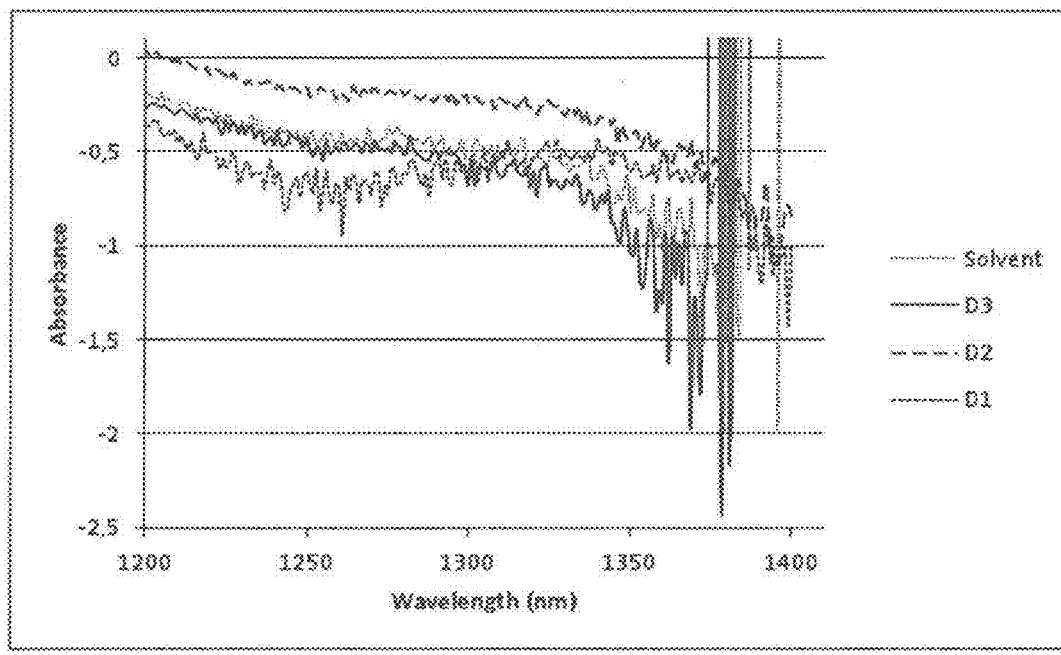

In FIG. 3 the overall absorbance spectra of proteins fingerprints are different in a concentration and temperature dependent manner as compared to FIG. 2. Whereas the absorbance spectra of D2 remains highest between 1200-1350 nm, in D1 the latter occurs between 1350-1400 nm compared to solvent and D3. This phenomenon is reversed at 1200-1300 nm. These variations show that the water molecules are arranged in a concentration and temperature dependence compared to FIG. 2. This means that the water absorption in near infrared (NIR) region is affected by protein concentration, where its dynamic is noticeable between D1, D2 and D3.

Figure 4:
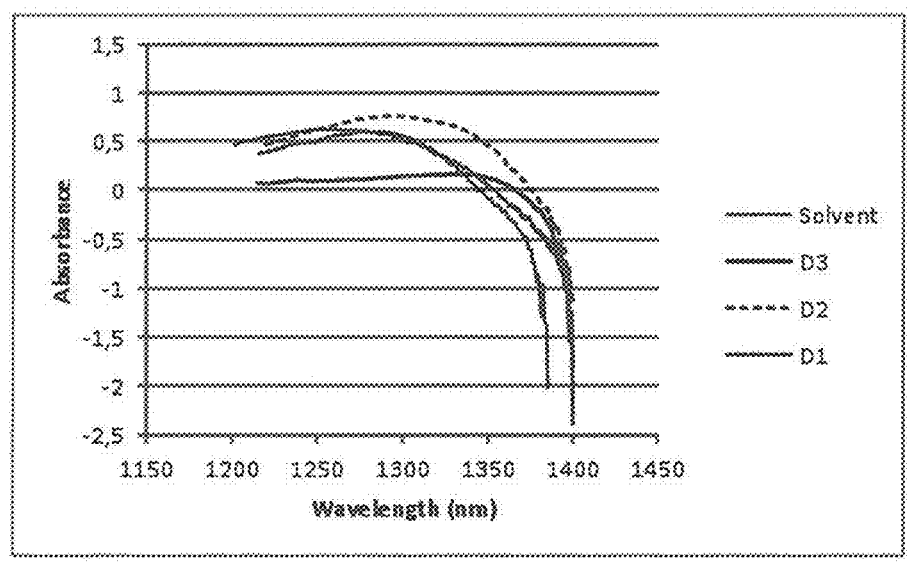

In FIG. 4 the overall absorbance spectra of proteins fingerprints are different in a concentration and temperature dependent manner as compared to FIG. 3. Whereas the absorbance spectrum of D2 is highest at 1250-1400 nm (compared to FIG. 3 1200-1350 nm), in D1 the latter is true between 1380-1400 nm compared to solvent and 1200-1350 nm compared to D3. The absorbance of D1 is relatively higher than solvent between 1350-1400 nm and lower between 1200-1350 nm. These variations show that the water molecules are arranged in a concentration and temperature (compared to FIGS. 2 and 3) dependent manner around the protein molecules. This means that the water absorption in NIR region is affected by protein concentration, where its dynamic is noticeable between D1, D2 and D3.

Figure 5:
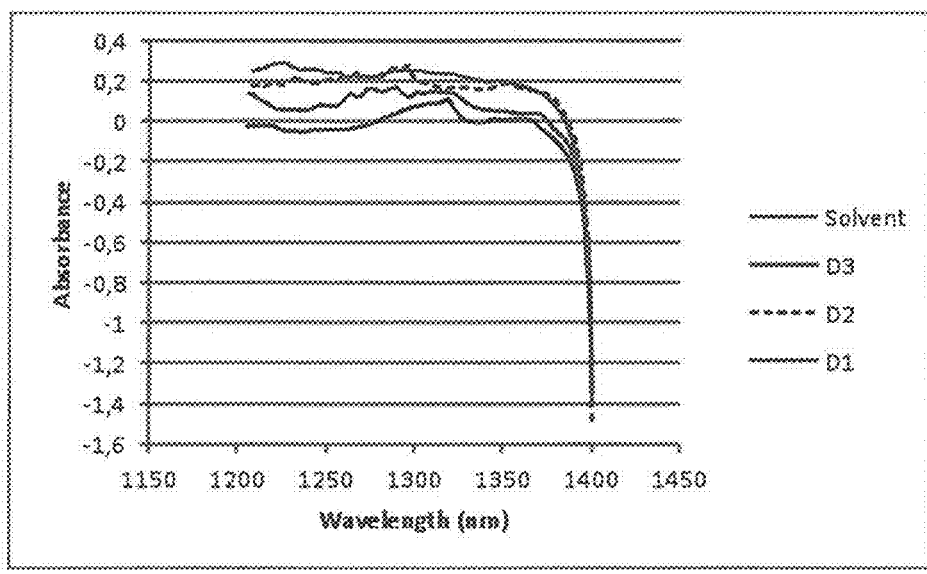

In FIG. 5 the overall spectra of proteins fingerprints are different in a concentration and temperature dependent manner as compared to FIGS. 3 and 4. Whereas the absorbance spectrum of D2 remains highest compare to D1 and D3, between 1200-1400 nm (compared to FIG. 4 1350-1400 nm), it remains lower than the absorbance spectrum of solvent. These variations show that the water molecules are arranged in a concentration and temperature (compared to FIGS. 2 to 4) dependent manner around the protein molecules. Yet these differences decree as the temperature rises. This means that the water absorption in NIR region is affected by protein concentration less than the temperature, as it is noticeable between D1, D2 and D3 in FIGS. 2 to 5.

Figure 6:
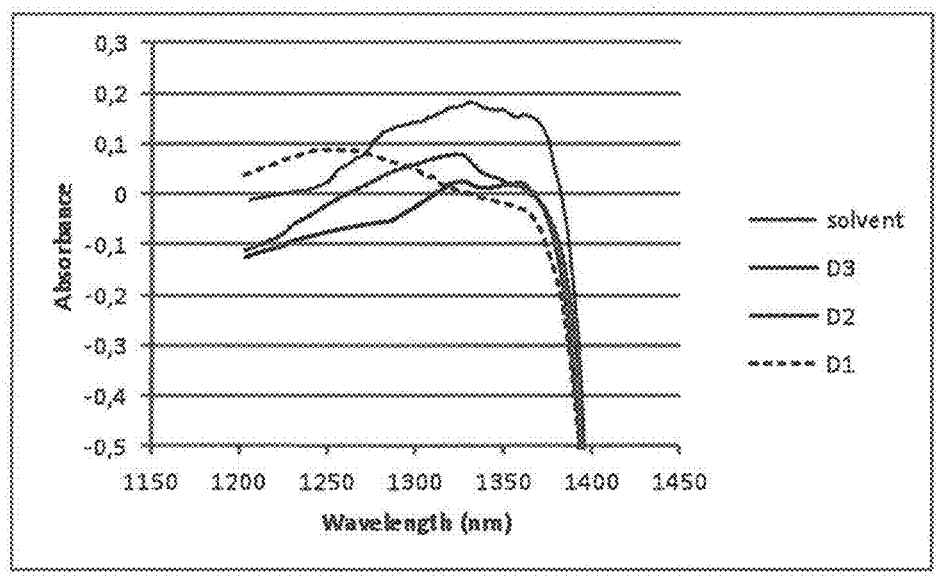

In FIG. 6 the overall absorbance spectra of proteins fingerprints are different in a concentration and temperature dependent manner as compared to FIGS. 3 to 5. Whereas the absorbance spectrum of D2 is lowest between 1300-1400 nm, compared to solvent D1 and D3, between 1200-1400 nm (compared to FIG. 4 1350-1400 nm), it remains highest between 1200-1250 nm. These variations show that the water molecules are arranged in a concentration and temperature (compared to FIGS. 2 to 5) dependent manner around the protein molecules. These differences are more noticeable as the temperature rises. This means that the water absorption in NIR region is affected by protein concentration less than the temperature as it is seen between D1, D2 and D3 in FIGS. 2 to 5.

Figure 7:
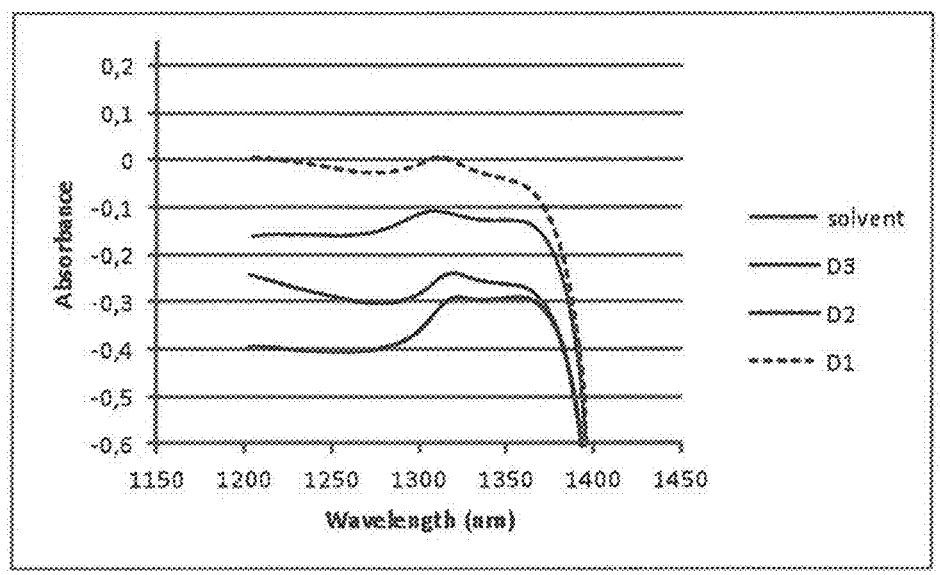

In FIG. 7 the overall absorbance spectra of proteins fingerprints are different in a concentration and temperature dependent manner as compared to FIGS. 3 to 6. Their morphologies remain similar. The absorbance spectrum of D3 is lowest between 1200-1400 nm, compare to solvent, D1 and D2. The absorbance spectrum of D1 is highest and increases as the wavelength decreases from 1450 to 1200 nm. These variations show that the water molecules are arranged in a concentration and temperature (compared to FIGS. 2 to 6) dependent manner around the protein molecules. These differences and evolution in spectral morphologies are more noticeable as the temperature rises. This means that the water absorption in NIR region is affected by protein concentration less than the temperature as it is seen between D1, D2 and D3 in FIGS. 2 to 6.

Figure 8:
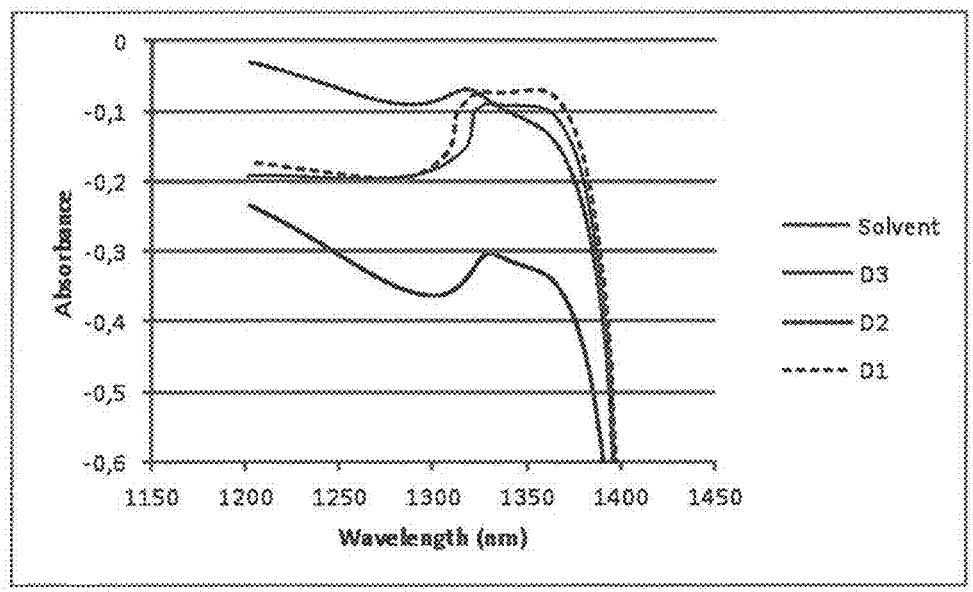

In FIG. 8 the overall absorbance spectra of proteins fingerprints for solvent and D1 are not different. There are clear differences pair wise between solvent, D1 and D2, D3 between 1200-1450 nm. The absorbance of both D2 and D3 are higher at 1200 nm compared to 1350 nm. It appears that these two independent absorbance changes are temperature dependent, especially for D3, compared to FIGS. 3 to 7. These variations show that the water molecules are arranged in a concentration and temperature (compared to FIGS. 2 to 7) dependent manner around the protein molecules. These differences and evolution in spectral morphologies are more noticeable as the temperature rises. This means that the water absorption in NIR region is affected by protein concentration less than the temperature as it is seen between D1, D2 and D3 in FIGS. 2 to 6.

Figure 9:
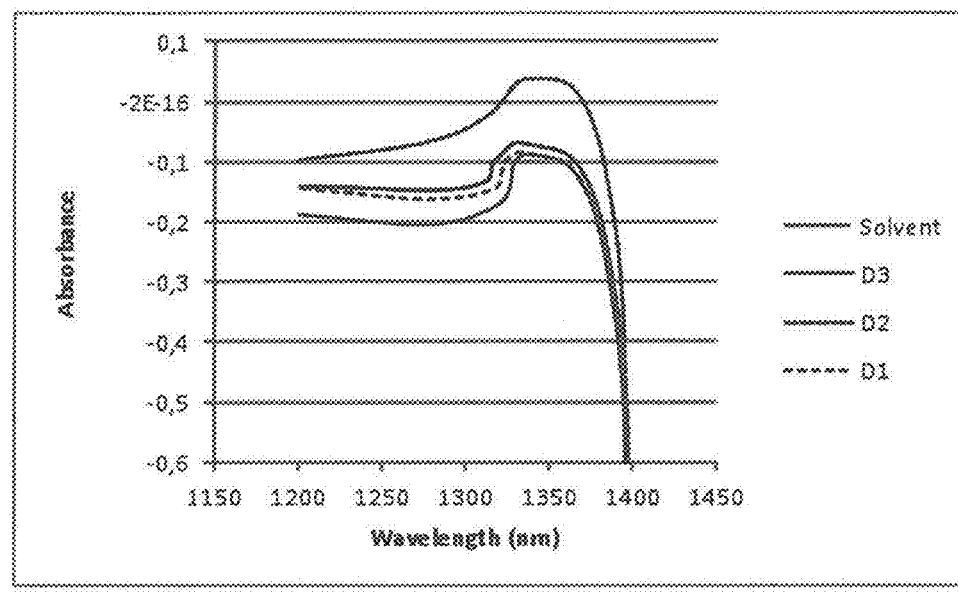

FIG. 9 shows a return to base line yet not completely. The overall absorbance spectra of proteins fingerprints for solvent D1 and D3 are not different (1200-1450 nm). Although spectral morphology of D2 has similarities with the others, its return to base line seems to be delayed or changed between 1200-1350 nm. Here the combination of change in temperature and the presence of the protein in this particular concentration prevent water molecules to return to their initial states. They have irreversibly changed position therefore their absorbance in NIR wavelength. This means that the water absorption in NIR wavelength is affected by protein concentration less than the temperature as it is seen between D1, D2 and D3 in FIGS. 2 to 6.

Figure 10:
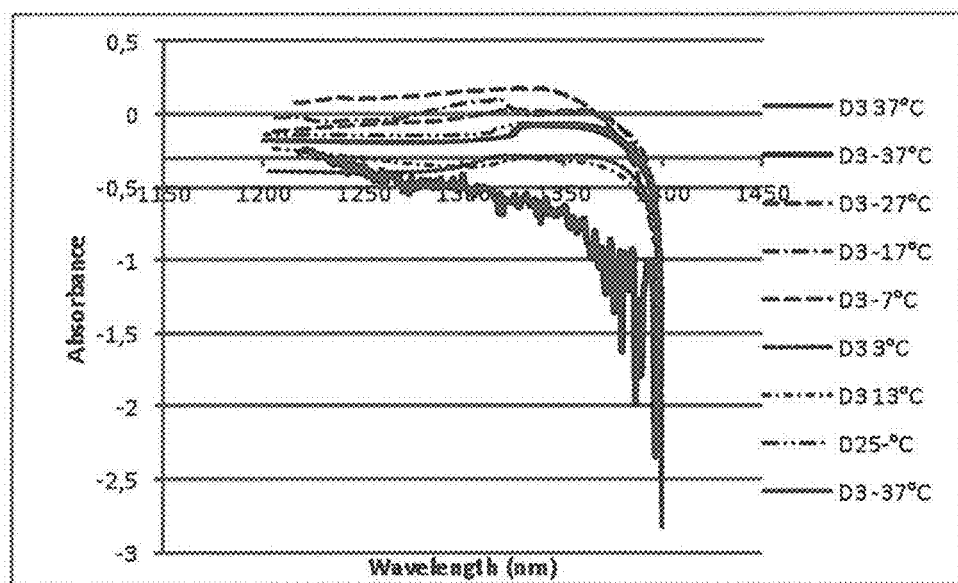

FIG. 10 shows the spectral evolution of protein assemblies according to the variation of temperature from 37° C. to −37° C. and back to 37° C. The spectral morphology is changing with temperature variation. This is due to the rearrangement and interaction of water molecules around the proteins in each temperature respectively. It means that the absorbance of water molecules making a solid fingerprint of proteins different conformations.

As one can see, protein conformations change depending on the protein concentration and temperature. The difference in this regard is more noticeable in FIG. 10 as the temperature spectral evolution is shown from −37° C. to 37° C.

Figure 11:
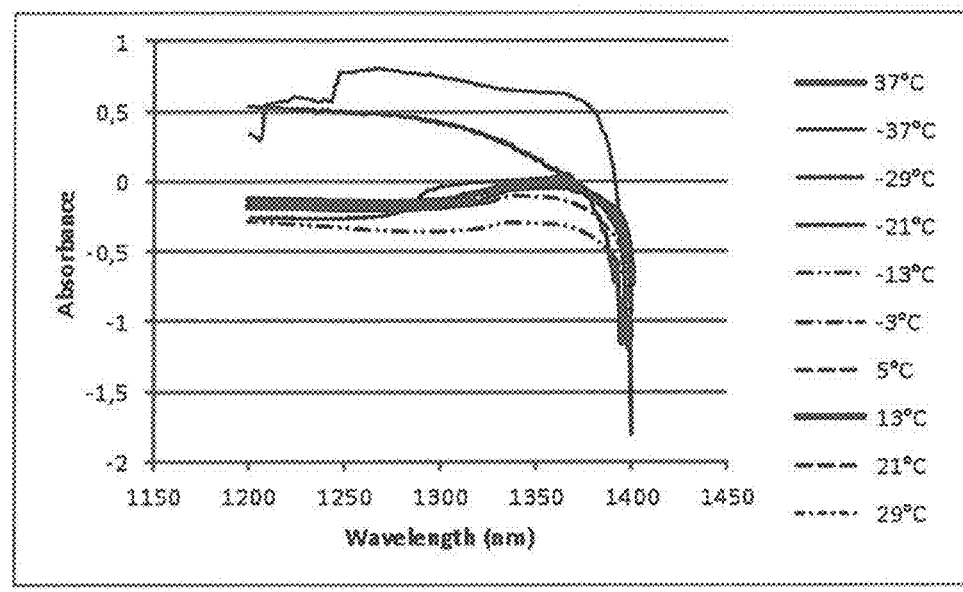
FIG. 11 shows results on rat hypothalamus extracts in presence of bithionol that disturbs the protein assemblies.

FIG. 11 shows results on rat hypothalamus extracts in presence of bithionol that disturbs the protein assemblies. Bithionol changes the protein conformation therefore it changes also water molecules spectra in NIR wavelength. The latter is noticed the most at −37° C. as compared to FIG. 3. The return to base line is fast. This means that bithionol induced conformation changes are visible in low temperature and reversible as the temperature rises. As shown in FIG. 11, bithionol disturbs the protein assemblies, the way that the protein conformation is adapted to the molecules presence and therefore gives a characteristic fingerprint.

Figure 12:
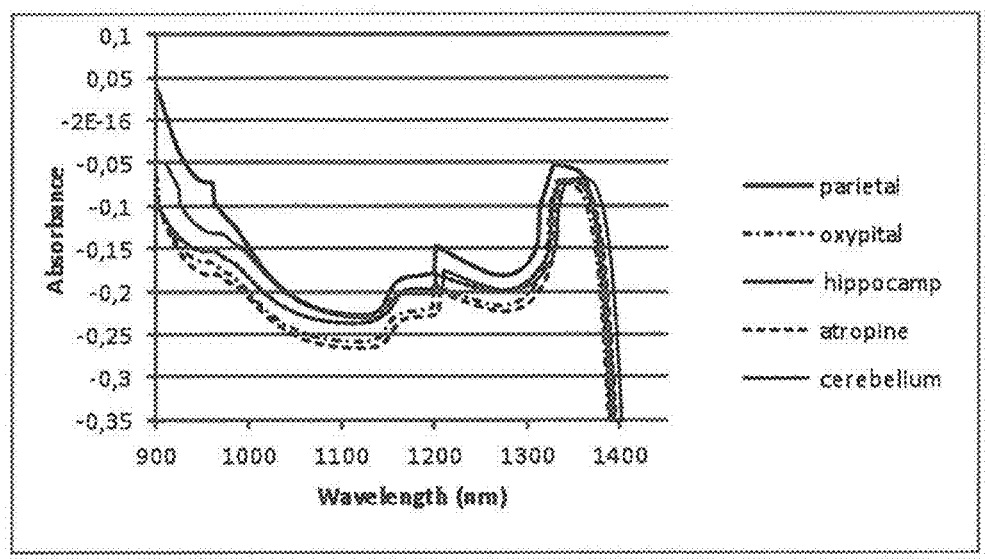
FIGS. 12 to 16 shows the interaction of atropine with a total protein extract of human cerebellum, occipital lobe and hippocampus.

FIG. 12 shows protein assemblies from different human brain structures in presence of atropine at 37° C. The spectral morphologies of different brain structures though following the same tendency are not similar in presence of atropine. The absorbance spectrum of protein from partial lob is higher between 900-1000 nm compared to the rest. The differences are not conclusive. This means that initial rearrangements of water molecules are not comparable between different human brain structures yet not enough to be noticed at 37° C.

Figure 13:
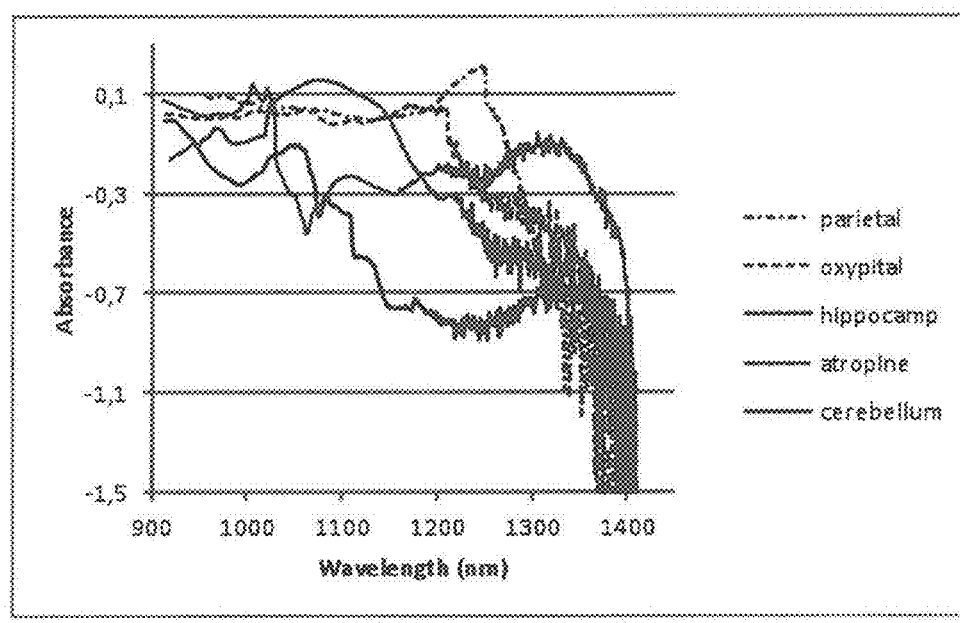

FIG. 13 shows protein assemblies from different human brain structures in presence of atropine at −37° C. There are huge differences between the absorbance spectra of different human brain structures in presence of atropine. Water molecules around cerebellum proteins absorb less between 1100-1400 nm where the one around parietal lob proteins absorbs the most. The water molecules arrangements are different in different brain structures, underlining their difference in structure and function. The latter is in favour of molecular conformation fingerprints and their corresponding physiological roles in human. This means that the fingerprints can be seen thanks to the change in temperature as compared to FIG. 12.

The protein assemblies in different human brain structure in presence of atropine are not the same. While at 37° C. these differences are not noticeable, they are highly different at −37° C. (FIGS. 12 and 13). Said changes are all following in a tissue dependent manner their specific dynamic pattern (FIGS. 14 and 15).

Figure 14:
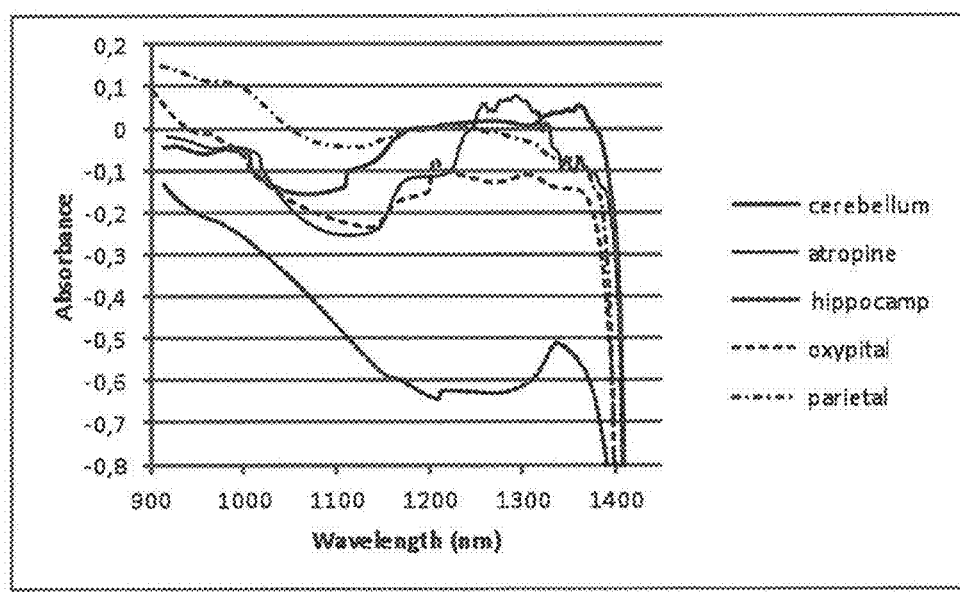

FIG. 14 shows protein assemblies from different human brain structures in presence of atropine at −7° C. Cerebellum proteins have changed in conformation as it can be seen through water molecules NIR spectra. It is highest between 1250-1400 nm. On the contrary hippocampus proteins effect on water rearrangements in presence of atropine is opposite of the one from cerebellum as they absorb less within the same wavelength range. This means that thanks to change in water molecule absorbance the fine conformational changes of proteins from different structures due to the presence of a drug can be studied.

Figure 15:
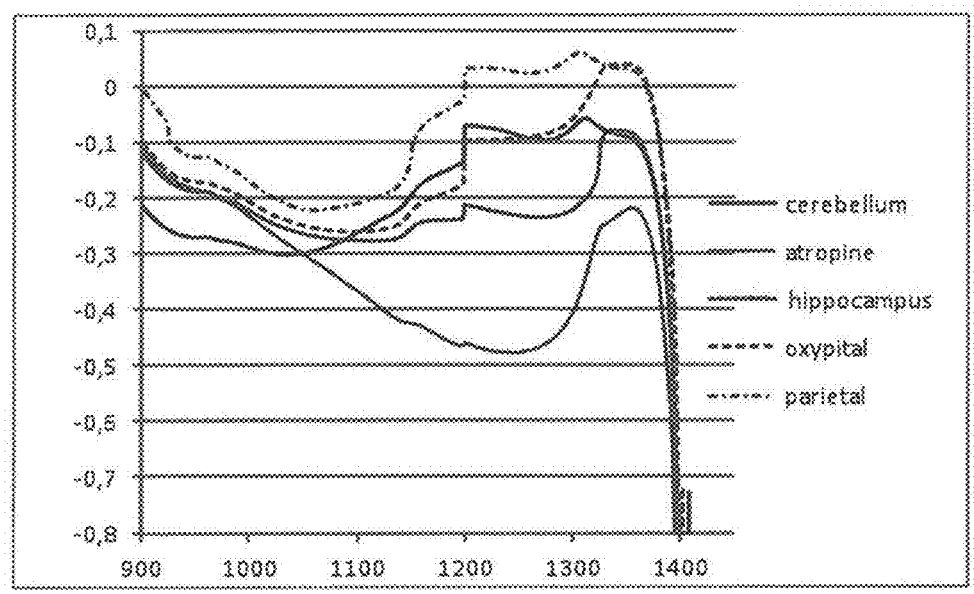

FIG. 15 shows protein assemblies from different human brain structures in presence of atropine at 7° C. Cerebellum proteins, in presence of atropine, have changed their conformation, as it can be seen through water molecules NIR spectra. It is highest between 1250-1400 nm. On the contrary hippocampus proteins effect on water rearrangements in presence of atropine is opposite to the one from cerebellum as they absorb less within the same wavelength range. This means that thanks to change in water molecule absorbance the fine conformational changes of proteins from different structures can be studied.

Figure 16:
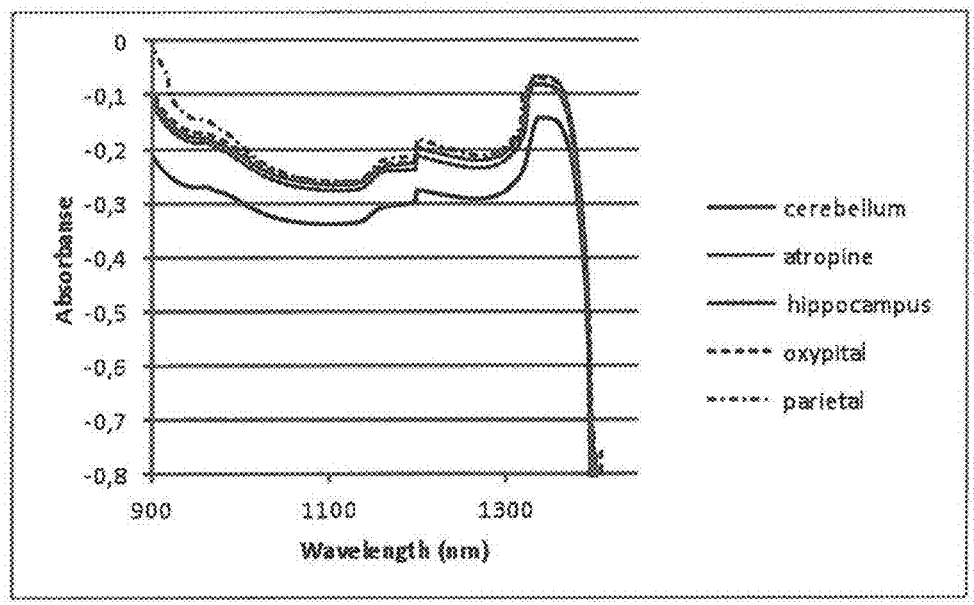

FIG. 16 shows protein assemblies from different human brain structures in presence of atropine at 37° C. Return to base line, although not exactly the same. The overall absorbance spectra at NIR wavelength are comparable but cerebellum is lower from the other. This means that atropine changes protein conformation differently from human cerebellum from the other brain structures (as it is highlighted after return to 37° C.) The latter is in line with already known muscarinic receptor distribution in different human brain tissue.

4) CONCLUSION

The dynamic spectroscopy provides a powerful exploration method that can easily be adapted to any kind of screening both for basic research and for applied pharmaceutical needs. It is simple and easy to handle. Thanks to its one step set up the experimental errors are minimized and its reproducibility increased. It is an out most adapted method for biomarker research, drug development, and personalized medicine in all area of medical research.

It is also a powerful technique for structural biology and chemistry.

Example of the Method According to the Invention Applied to a Clinical Trial Directed to Inflammatory Bowel Disease (IBD)

The clinical trial is directed to inflammatory bowel disease (IBD). The patients are followed according to standard clinical protocols for infliximab and their general conditions are assessed based on the MAYO scoring system. The method according to the invention aims to identify the responders and non-responders profile for infliximab (Remicad®) in a prospective study.

Patients

All the patients have a treatment: infliximab (Remicad®). infliximab is an anti-TNFalpha. 50 patients (women=16, men=34) with an average age of 43±8 year seeking medical assistance at Erlangen hospital day-care unit are taking part to the study. Patient's whole blood is collected using sodium citrate vacutainer tubes (5-10 ml/patient). Samples are blinded.

Sample Preparation

Peripheral blood mononuclear cells (PBMCs) are separated and isolated on ficoll gradient from blood samples, and then frozen. Crude PBMC membranes are prepared in physiological conditions without addition of any protease inhibitor or anti-phosphatase or lyses buffer. PBMC samples were subjected to three fast deep freezing (liquid nitrogen, slow thaw at 4° C., cycle. Determination of protein concentration: total protein concentration was determined using BCA assay (BCA Protein Assay Reagent, bicinchoninic acid).

Drug: infliximab was provided in lyophilized from and put in solution at 1 mg/ml using sterile double distilled milli-Q water.

Experiment

To both spectroscopy cells (sample and blank, respectively) 100 μl of HBSs and 10 μl of crude membrane proteins from each patient's PBMC (final concentration 0.01 mg/ml) was added. Baseline spectroscopy experiment was performed at 37° C. within a wavelength range of 850-1450 nm. This was followed with an experiment performed at −37° C., and then with increasing temperatures to 37° C. under the same wavelength interval. infliximab was added at final concentration 10e-6M to the test samples, before repeating the same experiment cycle. This was repeated three times for each patient's sample.

Results

One variable is analyzed in presence and in absence of infliximab: Compare Individual Macromolecular Volume (INV), that is defined as the total macromolecular spectral change from −37° C. to 37° C., due to the macromolecular conformational changes in absence and presence of a drug, expressed as change in absorbance as a function of wavelength and temperature. A small change in volume indicates a minor impact of the treatment, whereas a major change underlines their importance in macromolecular rearrangements and therefore higher probability for therapeutic effect. The results are shown in FIGS. 17 and 18.

Figure 17:
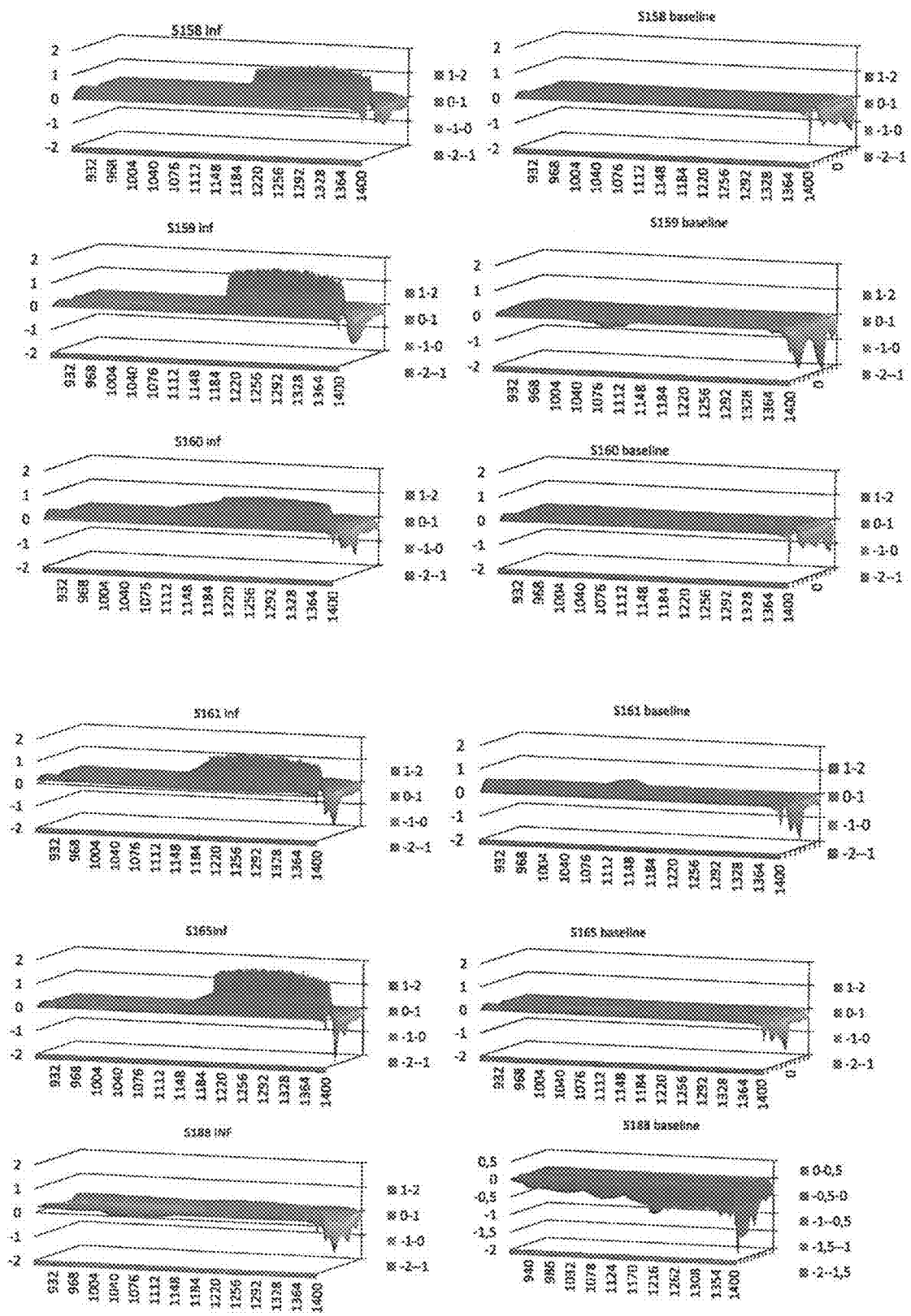
FIG. 17 shows outcomes of a method according to the invention applied to patients with IBD sensitive to a given drug

FIG. 17 shows INV profiles for responder samples to infliximab with axe y=absorbance, X=wavelength (nm) and Z=temperature (° C.).

Figure 18:
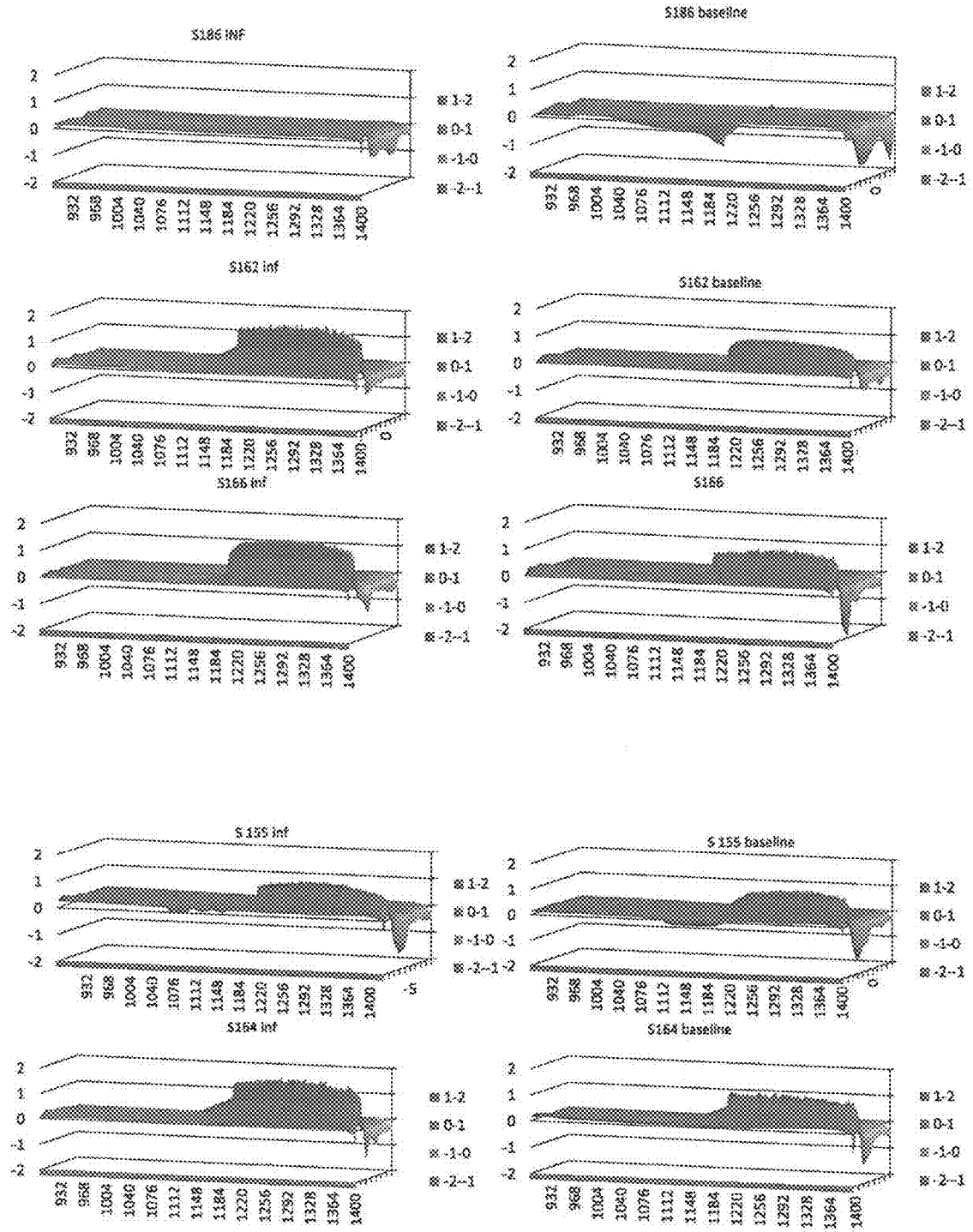
FIG. 18 shows outcomes of a the same method as in FIG. 17 applied to patients with IBD non-sensitive to a given drug.

FIG. 18 shows INV profiles for non-responder samples to infliximab (same axes as in FIG. 17)

Results are analyzed based on their spectral fingerprints going from −37° C. to 37° C. and compared to identify responders and non-responders patients.

They show that considering INV, it increases unanimously in presence of infliximab for patients responding to infliximab.

The patients samples identified as responders to infliximab are then compared to the MAYO scores of the patients within the clinical trial and there is a perfect correspondence between the list of patients being responsive to infliximab and the samples showing a significant change in their fingerprint spectra during the present experiment.

The further step is to choose characteristic biomarkers that differ between the responsive and non-responsive patients. Said biomarker will be able to be used as a characteristic of a responsive or a non-responsive patient to the treatment.

The invention claimed is:

1. Method for obtaining the fingerprint of at least one biological molecule of interest in a sample by spectroscopy under physiological conditions comprising:
   a) exposing the sample to a light source in the near infrared spectrum in the range of 680 nm to 1410 nm,
   b) measuring at various wavelengths the light intensity transmission of water molecules surrounding the biological molecule of interest, and
   c) determining the fingerprint of said biological molecule of interest,
   wherein several fingerprints are taken at different temperatures including negative temperatures (° C.) and compiled to deduct a dynamical conformational comportment of the biological molecule of interest.

2. Method according to claim 1, wherein outcomes are measured within a temperature range between −37° C. and 37° C.

3. Method according to claim 2, wherein one fingerprint is realized for each integer degree of the range.

4. Method for the determination of the conformation of at least one biological molecule in a sample using spectroscopy under physiological conditions, comprising:
   a) determining the fingerprint of the biological molecule of interest according to the method of claim 1, and
   b) determining from the outcomes of step a) the conformation of said molecule of interest.

5. Method for the determination of the biological activity of at least one molecule of interest, comprising:
   a) putting in contact the sample with a test molecule,
   b) determining the fingerprint of the sample containing the test molecule as defined in a) according to the method of claim 1,
   c) repeating step a) and b) with at least two different samples;
   d) comparing the fingerprints obtained in b) and c), and
   e) deducting the biological activity of the molecule of interest.

6. Method according to claim 5, comprising the following steps:
   a) determining a fingerprint of the test molecule in solution;
   b) putting in contact the sample with a test molecule;
   c) determining the fingerprint of the sample containing the test molecule as defined in a);
   d) repeating step b) and c) with at least two different samples;
   e) comparing the fingerprints obtained in a), c) and d); and f) deducting the biological activity of the molecule of interest.

7. Method for the determination of the biological activity of at least one molecule of interest according to claim 5, comprising:
   a) putting in contact the sample with a test molecule,
   b) determining the fingerprint of the sample containing the test molecule as defined in a);
   c) repeating step a) and b) with at least two different samples;
   d) comparing the fingerprints obtained in b) and c), and
   e) deducting the biological activity of the molecule of interest.

8. The method according to claim 4, wherein the sample is selected from a tissue extract or an organ extract.

9. The method of claim 8, wherein the sample is a brain extract.

10. An in vitro method for identification of a patient sensitivity to a treatment with a given drug, said method comprising:
   a) dividing a sample of a patient suspected to suffer or being prone to suffer from a given disease, in two subsamples A and B,
   b) determining the fingerprint of subsample A according to claim 1,
   c) putting in contact subsample B with the given drug,
   d) determining the fingerprint of subsample obtain through step c),
   e) determining that the patient is sensitive to the given drug if the fingerprint obtained in d) shows a change of individual macromolecular volume relative to the control level determined in b).

11. A method to select at least a biomarker indicative of a patient sensitivity to a treatment with a given drug, comprising:
   a) determining a group of patients sensitive to the given drug according to claim 10,
   b) determining a group of patients non-sensitive to the given drug according to claim 10,
   c) measuring various biomarkers in the patients of group a),
   d) measuring various biomarkers in the patients of group b),
   e) selecting at least a biomarker for which the measure under c) increases or decreases in comparison with the measure under d) as a biomarker indicative of a patient sensitivity to a treatment with said given drug.

12. A method for improving treatment effect in a patient suffering from a given disease, said method comprising:
   (a) determining a patient's sensitivity to a given drug according to claim 10; and
   (b) administrating said given drug to said patient.

13. A method, according to claim 10 wherein said drug is an anti-TNF alpha antibody.

14. A method, according to claim 10 wherein said disease is inflammatory bowel disease.

15. The method according to claim 8, wherein the sample is a sample of peripheral blood molecular cells.

16. Method according to claim 1, wherein the near infrared spectrum is in the range of 900 to 1410 nm.

17. Method according to claim 1, wherein the near infrared spectrum is in the range of 680 to 1100 nm.

* * * * *